United States Patent
Krieger et al.

(10) Patent No.: US 6,878,825 B2
(45) Date of Patent: Apr. 12, 2005

(54) RYLENE DERIVATIVES AND THEIR USE AS DYES

(75) Inventors: Matthias Krieger, Mannheim (DE); Arno Böhm, Mannheim (DE); Erik Reuther, Mainz (DE); Klaus Müllen, Cologne (DE)

(73) Assignees: BASF Aktiengesellschaft, Ludwigshafen (DE); Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 10/468,601
(22) PCT Filed: Feb. 14, 2002
(86) PCT No.: PCT/EP02/01556
§ 371 (c)(1), (2), (4) Date: Aug. 20, 2003
(87) PCT Pub. No.: WO02/066438
PCT Pub. Date: Aug. 29, 2002

(65) Prior Publication Data
US 2004/0068114 A1 Apr. 8, 2004

(30) Foreign Application Priority Data
Feb. 20, 2001 (DE) ................................ 101 08 156

(51) Int. Cl.⁷ ............... C07D 221/18; C09B 3/14
(52) U.S. Cl. ............... 546/28; 106/498; 106/499; 546/26
(58) Field of Search ............... 546/28, 26, 38; 106/498, 499

(56) References Cited

U.S. PATENT DOCUMENTS

| 4,599,408 A | 7/1986 | Spietschka et al. |
| 5,808,073 A * | 9/1998 | Bohm et al. ............ 546/39 |

FOREIGN PATENT DOCUMENTS

| DE | 0 596 292 | 5/1994 |
| DE | 43 38 784 | 5/1995 |
| DE | 195 12 773 | 10/1996 |
| EP | 0 636 666 | 2/1995 |
| WO | 96/22332 | 7/1996 |

OTHER PUBLICATIONS

H. Langhals et al.: "A two–step synthesis of quaterrylene-tetracarboxylic bismides–novel NIR fluorescent dyes" Tetrahedron Letters, vol. 36, No. 36, pp. 6423–6424.
Chimia, vol. 48, pp. 503–505.
Dyes and Pigments, vol. 16, pp. 19–25 1991.

* cited by examiner

Primary Examiner—Charanjit S. Aulakh
(74) Attorney, Agent, or Firm—Oblon, Spivak, McClelland, Maier & Neustadt, P.C.

(57) ABSTRACT

Rylene derivatives of the general formula I

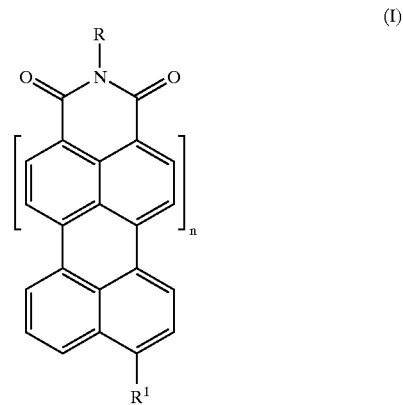

where the variables have the following meanings:
R is hydrogen or substituted or unsubstituted $C_1-C_{30}$-alkyl, aryl or hetaryl;
$R^1$ is hydrogen or bromine;
$R^2$ is hydrogen or $C_1-C_6$-alkyl;
$R^3$ is hydrogen, $C_1-C_{18}$-alkyl or substituted or unsubstituted aryl or hetaryl; and
n is 2 or 3.

12 Claims, No Drawings

RYLENE DERIVATIVES AND THEIR USE AS DYES

The present invention relates to novel rylene derivatives of the general formula I

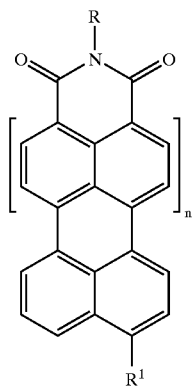

where the variables have the following meanings:

R is hydrogen;
  $C_1$–$C_{30}$-alkyl, whose carbon chain may be interrupted by one or more —O—, —S—, —$NR^2$—, —CO— and/or —SO— groups and which may be monosubstituted or polysubstituted by carboxyl, sulfo, hydroxyl, cyano, $C_1$–$C_6$-alkoxy and/or by a 5- to 7-membered heterocyclic radical which is bonded via a nitrogen atom, may contain further heteroatoms and may be aromatic;
  aryl or hetaryl, each of which may be monosubstituted or polysubstituted by $C_1$–$C_{18}$-alkyl, $C_1$–$C_6$-alkoxy, halogen, hydroxyl, cyano, carboxyl, —$CONHR^3$, —$NHCOR^3$ and/or aryl- or hetarylazo, each of which may be substituted by $C_1$–$C_{10}$-alkyl, $C_1$–$C_6$-alkoxy, halogen, hydroxyl, cyano and/or carboxyl;

$R^1$ is hydrogen or bromine;

$R^2$ is hydrogen or $C_1$–$C_6$-alkyl;

$R^3$ is hydrogen; $C_1$–$C_{18}$-alkyl; aryl or hetaryl, each of which may be substituted by $C_1$–$C_8$-alkyl, $C_1$–$C_6$-alkoxy, halogen, hydroxyl and/or cyano; and n is 2 or 3, and to the preparation of the rylene derivatives I and to their use for coloring high-molecular-weight organic and inorganic materials, in particular plastics, surface coatings and printing inks, as dispersion aids, pigment additives for organic pigments and intermediates for the preparation of fluorescent colorants and pigment additives, as coloring components in decorative cosmetics, for the preparation of aqueous polymer dispersions which are colored or absorb and/or emit in the near infrared region of the electromagnetic spectrum, as photoconductors in electrophotography, as emitters in electroluminescence and chemiluminescence applications, as active components in fluorescence conversion and as laser dyes.

In addition, the invention relates to novel rylenetetracarboxylic monoimide monoanhydrides of the general formula III

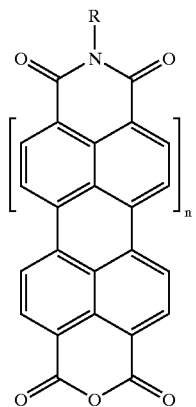

where the variables are as defined above, as intermediates for the preparation of the rylene derivatives I, and to their preparation and use for coloring high-molecular-weight organic and inorganic materials, as dispersion aids, pigment additives for organic pigments and intermediates for the preparation of polymerizable colorants and pigment additives, as coloring components in decorative cosmetics, for the preparation of aqueous polymer dispersions which are colored or absorb and/or emit in the near infrared region of the electromagnetic spectrum, as photoconductors in electrophotography, as emitters in electroluminescence and chemiluminescence applications, as active components in fluorescence conversion and as laser dyes.

Shorter rylene-3,4-dicarboximides (where n=0 or 1 in the formula I, i.e. corresponding naphthalene and perylene derivatives) are known. Perylene-3,4-dicarboximides which are unsubstituted or substituted by halogen in the peri position (9 position of the perylene structure) are described, for example, in EP-A-636 666, in Chimia 48, pp. 503–505 (1994), in EP-A-592 292 and in Dyes and Pigments 16, pp. 19–25 (1991). Further 9-haloperylene-3,4-dicarboximides which are additionally substituted in the perylene structure are disclosed in WO-A-96/22332. A common feature of the known compounds is that they absorb in the near UV or the short-wave region of the visible spectrum, i.e. essentially in the range from 340 to 540 nm.

It is an object of the present invention to provide rylene derivatives which absorb and emit in the long-wave, i.e. in the red and infrared, region of the electromagnetic spectrum and can be specifically derivatized in the peri position.

We have found that this object is achieved by the terrylene and quaterrylene derivatives of the formula I defined at the outset.

Preferred rylene derivatives are defined in the sub-claim.

We have also found a process for the preparation of the rylene derivatives I, which comprises a) monohydrolyzing an asymmetrical rylenetetracarboxylic diimide of the general formula II

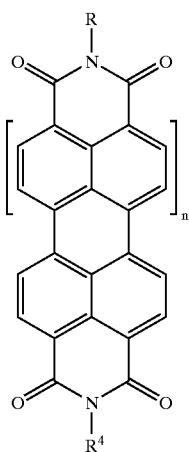

where $R^4$ is $C_5$–$C_8$-cycloalkyl, whose carbon skeleton may be interrupted by one or more —O—, —S— and/or —$NR^2$— groups and which may be monosubstituted or polysubstituted by $C_1$–$C_6$-alkyl, under alkaline conditions in the presence of a polar organic solvent, b) monodecarboxylating the rylenetetracarboxylic monoimide monoanhydride of the general formula III

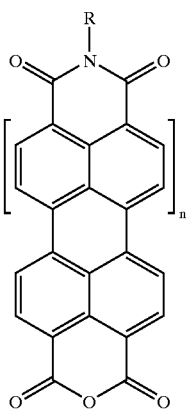

formed in step a) in the presence of a tertiary nitrogen-basic compound and in the presence of a transition-metal catalyst, and c) if desired, subsequently reacting the reaction product with elemental bromine.

We have also found a process for the preparation of the rylenetetracarboxylic monoimide monoanhydrides III, which comprises monohydrolyzing an asymmetrical rylene-tetracarboxylic diimide II under alkaline conditions in the presence of a polar organic solvent.

We have also found the rylenetetracarboxylic monoimide monoanhydrides of the formula III defined at the outset as intermediates for the rylene-3,4-dicarboximides I.

Not least, we have also found the applications likewise mentioned at the outset for the rylene derivatives I and the rylenetetracarboxylic monoimide monoanhydrides III.

All the alkyl groups which occur in the formulae I to III may be straight-chain or branched. If the alkyl groups are substituted, they generally carry one or two substituents.

Specific examples which may be mentioned of suitable radicals R, $R^1$, $R^2$, $R^3$ and $R^4$ (or substituents thereof) are the following:

methyl, ethyl, propyl, isopropyl, butyl, isobutyl, tert-butyl, pentyl, isopentyl, neopentyl, tert-pentyl, hexyl, 2-methylpentyl, heptyl, 1-ethylpentyl, octyl, 2-ethylhexyl, isooctyl, nonyl, isononyl, decyl, isodecyl, undecyl, dodecyl, tridecyl, isotridecyl, tetradecyl, pentadecyl, hexadecyl, heptadecyl, octadecyl, nonadecyl and eicosyl (the above names isooctyl, isononyl, isodecyl and isotridecyl are trivial names and originate from the alcohols obtained by the oxo synthesis);

2-methoxyethyl, 2-ethoxyethyl, 2-propoxyethyl, 2-isopropoxyethyl, 2-butoxyethyl, 2- and 3-methoxypropyl, 2- and 3-ethoxypropyl, 2- and 3-propoxypropyl, 2- and 3-butoxypropyl, 2- and 4-methoxybutyl, 2- and 4-ethoxybutyl, 2- and 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-isopropylthioethyl, 2-butylthioethyl, 2- and 3-methylthiopropyl, 2- and 3-ethylthiopropyl, 2- and 3-propylthiopropyl, 2- and 3-butylthiopropyl, 2- and 4-methylthiobutyl, 2- and 4-ethylthiobutyl, 2- and 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithiaundecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethylaminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-diazaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

propan-2-on-1-yl, butan-3-on-1-yl, butan-3-on-2-yl and 2-ethylpentan-3-on-1-yl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylpropyl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 3-hydroxypropyl, 1-hydroxyprop-2-yl, 2- and 4-hydroxybutyl, 1-hydroxybut-2-yl and 8-hydroxy-4-oxaoctyl;

cyanomethyl, 2-cyanoethyl, 3-cyanopropyl, 2-methyl-3-ethyl-3-cyanopropyl, 7-cyano-7-ethylheptyl and 4,7-dimethyl-7-cyanoheptyl;

methoxy, ethoxy, propoxy, isopropoxy, butoxy, isobutoxy, sec-butoxy, tert-butoxy, pentoxy, isopentoxy, neopentoxy, tert-pentoxy and hexoxy;

carbamoyl, methylaminocarbonyl, ethylaminocarbonyl, propylaminocarbonyl, butylaminocarbonyl, pentylaminocarbonyl, hexylaminocarbonyl, heptylaminocarbonyl, octylaminocarbonyl, nonylaminocarbonyl, decylaminocarbonyl and phenylaminocarbonyl;

formylamino, acetylamino, propionylamino and benzoylamino;

chlorine, bromine and iodine;

phenylazo, 2-naphthylazo, 2-pyridylazo and 2-pyrimidylazo;

phenyl, 2-naphthyl, 2- and 3-pyrryl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3,5-triazyl), 6-quinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

2-, 3- and 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl and 2,4,6-tri-sec-butylphenyl, 2-, 3- and 4-tert-butylphenyl, 2,4-, 2,5-, 3,5- and 2,6-di-tert-butylphenyl, 2,4,6-tri-tert-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-chlorophenyl, and 2,4-, 2,5-, 3,5- and 2,6-dichlorophenyl; 2-, 3- and 4-hydroxyphenyl and 2,4-, 2,5-, 3,5- and 2,6-dihydroxyphenyl; 2-, 3- and 4-cyanophenyl; 3- and 4-carboxyphenyl; 3- and 4-carboxamidophenyl, 3- and 4-N-methylcarboxamidophenyl and 3- and 4-N-ethylcarboxamidophenyl; 3- and 4-acetylaminophenyl, 3- and 4-propionylaminophenyl and 3- and 4-butyrylaminophenyl; 3- and 4-N-phenylaminophenyl, 3- and 4-N-(o-tolyl)aminophenyl, 3- and 4-N-(m-tolyl)aminophenyl and 3- and 4-N-(p-tolyl)aminophenyl; 3- and 4-(2-pyridyl)aminophenyl, 3- and 4-(3-pyridyl)aminophenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthylazo)phenyl, 4-(2-pyridylazo)phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec-butylcyclohexyl, 3- and 4-tert-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec-butylcycloheptyl, 3- and 4-tert-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl, 2-dioxanyl, 4-morpholinyl, 2- and 3-tetrahydrofuryl, 1-, 2- and 3-pyrrolidinyl and 1-, 2-, 3- and 4-piperidyl.

The rylene derivatives I can advantageously be prepared by the multistep process according to the invention, in which, in step a), an asymmetrical rylenetetracarboxylic diimide II which is substituted by a cycloalkyl radical on an imide nitrogen is monohydrolyzed, and, in step b), the rylenetetracarboxylic monoimide monoanhydride III formed is monodecarboxylated. If a rylene derivative I which is brominated in the peri position ($R^1$=Br) is desired, a rylene derivative I which is unsubstituted in the peri position ($R^1$=H) is reacted with elemental bromine in a further step c).

Step a) of the process according to the invention, the hydrolysis of the cycloalkyl-substituted imide group of the rylenetetracarboxylic diimides II, is carried out in the presence of a polar organic solvent and in the presence of a base.

The asymmetrical rylenetetracarboxylic diimides II employed as starting materials for this purpose are known and can be prepared as described in EP-A-592 292 and in Chem. Eur. Journal 3, pp. 219–225 (1997).

Suitable solvents are, in particular, branched $C_3$–$C_6$-alcohols, such as isopropanol, tert-butanol and 2-methyl-2-butanol.

In general, from 40 to 200 g of solvent are used per g of II.

Suitable bases are inorganic bases, in particular alkali metal and alkaline earth metal hydroxides, for example sodium hydroxide and potassium hydroxide, which are preferably used in the form of aqueous solutions or suspensions (in general from 50 to 80% strength by weight), and organic bases, in particular alkali metal and alkaline earth metal alkoxides, preferably sodium alkoxides and potassium alkoxides, such as sodium methoxide, potassium methoxide, potassium isopropoxide and potassium tert-butoxide, which are usually employed in anhydrous form.

In general, from 5 to 50 equivalents of base, based on II, are required.

The reaction temperature is generally from 50 to 120° C., preferably from 60 to 100° C.

The hydrolysis is usually complete in from 10 to 40 hours. Step a) of the process is advantageously carried out as follows:

A suspension of rylenetetracarboxylic diimide II, base and solvent is heated to the desired reaction temperature with vigorous stirring. When the hydrolysis is complete and the mixture has been cooled to room temperature, a pH of from 1 to 4 is established using an acid, for example an inorganic acid, such as hydrochloric acid, or an organic acid, such as acetic acid. The product is filtered off, washed with hot water and subsequently dried at about 100° C. under reduced pressure.

In general, the rylenetetracarboxylic monoimide monoanhydride III obtained in step a) already has such a high assay (>90%) that it can be employed directly for the decarboxylation in step b).

In step b) of the process according to the invention, the rylenetetracarboxylic monoimide monoanhydrides III are monodecarboxylated in the presence of a tertiary nitrogen-basic compound as solvent and in the presence of a transition metal catalyst.

Suitable solvents are, in particular, high-boiling nitrogen bases, for example cyclic amides, such as N-methylpyrrolidone, and aromatic heterocyclic compounds, such as quinoline, isoquinoline and quinaldine.

The usual amounts of solvent are from 20 to 150 g per g of III.

Suitable catalysts are, in particular, the transition metals copper and zinc and especially also their inorganic and organic salts, which are preferably employed in anhydrous form.

Examples of preferred salts are copper(I) oxide, copper (II) oxide, copper(I) chloride, copper(II) acetate, zinc acetate and zinc propionate, particular preference being given to copper(I) oxide and zinc acetate.

It is of course also possible to use mixtures of said catalysts.

In general, from 50 to 90 mol % of catalyst, based on III, are employed.

The reaction temperature is generally from 100 to 250° C., in particular from 160 to 200° C. It is advisable to use a protective-gas atmosphere (for example nitrogen).

The decarboxylation is usually complete in from 3 to 20 hours.

Step b) of the process is advantageously carried out as follows:

A mixture of rylenetetracarboxylic monoimide monoanhydride III, solvent and catalyst is heated to the desired reaction temperature with stirring. When the decarboxylation is complete and the mixture has been cooled to room temperature, the reaction mixture is poured into approximately the same volume of a low-boiling alcohol, for example methanol, the same amount of a dilute inorganic acid, for example 5–6% strength by weight hydrochloric acid, is added with stirring, and the product is filtered off. If desired, the crude product is stirred in a suitable solvent, for example an aromatic solvent, such as xylene, filtered, washed with a low-boiling alcohol and dried at about 75° C. under reduced pressure.

Further purification is possible by recrystallization from a high-boiling solvent, for example N-methylpyrrolidone. In general, this is not necessary since the rylene derivatives I obtained ($R^1$=H) already have an assay of ≧95%.

For the preparation of the rylene derivatives I which are brominated in the peri position ($R^1$=Br), the unsubstituted rylene derivatives I can be subjected to step c) according to the invention, regioselective bromination.

This bromination is preferably carried out in an aliphatic monocarboxylic acid, in particular a $C_1$–$C_4$-carboxylic acid, such as formic acid, acetic acid, propionic acid, butyric acid or mixtures thereof, or in a halogenated, aliphatic or aromatic solvent, such as methylene chloride, chloroform or chlorobenzene.

From 5 to 30 g, preferably from 15 to 25 g, of solvent are usually employed per g of I to be brominated.

In general, the presence of a halogenation catalyst is not necessary. However, if it is desired to accelerate the bromination reaction (by a factor of approximately from 1.5 to 2), it is advisable to add elemental iodine, preferably in an amount of from 1 to 5 mol %, based on I.

In general, the molar ratio between bromine and I is from about 1:1 to 5:1, preferably from 3:1 to 4:1.

The reaction temperature is generally from 0 to 70° C., in particular from 10 to 40° C.

Depending on the reactivity of the substrate I and the presence or absence of iodine, the bromination is usually complete in from 2 to 12 hours.

Step c) of the process is advantageously carried out as follows:

A mixture of the rylene derivative I to be brominated and solvent is brought to the desired reaction temperature over the course of from 15 to 30 minutes with stirring, catalyst is added if desired, the desired amount of bromine is subsequently added over the course of from 5 to 10 minutes, and the mixture is stirred at the reaction temperature for from 2 to 12 hours with exclusion of light. After excess bromine has been removed using a vigorous stream of nitrogen, the reaction mixture is introduced into approximately the same amount of an aliphatic alcohol, for example methanol, and stirred overnight, and the precipitated product is filtered off, washed, preferably with the same alcohol, and dried at about 120° C. under reduced pressure.

In general, the brominated rylene derivatives I obtained in step c) also already have such a high assay (>95%) that they can be employed directly for the desired application.

The rylene derivatives I according to the invention are highly suitable for homogeneous coloring of high-molecular-weight organic and inorganic materials, in particular, for example, plastics, especially thermoplastics, surface coatings and printing inks, and oxidic layer systems.

They are also suitable as dispersion aids, pigment additives for organic pigments and intermediates for the preparation of fluorescent colorants and pigment additives, as coloring components in decorative cosmetics, for the preparation of aqueous polymer dispersions which are colored or absorb and/or emit in the near infrared region of the electromagnetic spectrum, and as photoconductors in electrophotography, as emitters in electroluminescence and chemiluminescence applications, as active components in fluorescence conversion and as laser dyes.

The rylenetetracarboxylic monoimide monoanhydrides III serving as intermediates for the rylene derivatives I can themselves also be used for coloring the above-mentioned high-molecular-weight organic and inorganic materials, as dispersion aids, pigment additives for organic pigments and intermediates for the preparation of polymerizable colorants and pigment additives, as coloring components in decorative cosmetics, for the preparation of aqueous polymer dispersions which are colored or absorb and/or emit in the near infrared region of the electromagnetic spectrum, and as photoconductors in electrophotography, as emitters in electroluminescence and chemiluminescence applications, as active components in fluorescence conversion and as laser dyes.

EXAMPLES

A) Preparation of Rylenetetracarboxylic Monoimide Monohydrides of the Formula III According to the Invention Examples 1 to 6

10 g (x mmol) of rylenetetracarboxylic diimide II were introduced into 500 ml of isopropanol, and a mixture of 40 g of potassium hydroxide and 30 ml of water was added. The mixture was then refluxed for t hours with stirring.

After it had been cooled to room temperature, the reaction mixture was introduced into 300 ml of a mixture of two parts by volume of water and one part by volume of concentrated hydrochloric acid. After the mixture had been stirred for 30 minutes, the product was filtered off, washed with water to pH neutrality and dried at 100° C. under reduced pressure.

Further details on these experiments and their results are shown in Table 1.

TABLE 1

| Ex. | x [mmol] | Rylenetetracarboxylic diimide II | t [h] | Yield [g]/[%] | Appearance | m.p. [° C.] |
|---|---|---|---|---|---|---|
| 1 | 13.2 | N-(2,6-Diisopropylphenyl)-N'-cyclohexylterylene-3,4:11,12-tetracarboxylic diimide | 20 | 8.9/100 | Blue-violet, microcrystalline | >350 |
| 2 | 14.2 | N-(p-Methoxyphenyl)-N'-cyclohexylterrylene-3,4:11,12-tetracarboxylic diimide | 28 | 8.4/95 | Black-blue, amorphous | >350 |
| 3 | 13.1 | N-Dodecyl-N'-cyclohexylterrylene-3,4:11,12-tetracarboxylic diimide | 18 | 8.7/97 | Black, amorphous | >350 |
| 4 | 11.4 | N-(2,6-Diisopropylphenyl)-N'-cyclohexylquaterrylene-3,4:13,14-tetracarboxylic diimide | 15 | 8.9/98 | Black, microcrystalline | >350 |
| 5 | 12.1 | N-(p-Methoxyphenyl)-N'-cyclohexylquaterrylene-3,4:13,14-tetracarboxylic diimide | 20 | 8.3/92 | Violet-black, amorphous | >350 |
| 6 | 11.3 | N-Dodecyl-N'-cyclohexylquaterrylene-3,4:13,14-tetracarboxylic diimide | 28 | 8.6/95 | Violet-black, amorphous | >350 |

B) Preparation of Rylene Derivatives I According to the Invention ($R^1$=H)

Examples 7 to 12

A mixture of x g (7 mmol) of rylenetetracarboxylic monoanhydride III and 7 g of copper(I) oxide in 400 ml of quinoline was heated to 220° C. with stirring and held at this temperature for t hours.

After it had been cooled to room temperature, the reaction solution was introduced into 400 ml of methanol, and 400 ml of a mixture of 3 parts by volume of water and 1 part by volume of concentrated hydrochloric acid were added. After the mixture had been stirred for 30 minutes, the product was filtered off, washed with water to pH neutrality and dried at 75° C. under reduced pressure. The crude product obtained in this way was subsequently freed from traces of the starting material by recrystallization from N-methylpyrrolidone.

Further details on these experiments and their results are shown in Table 2.

Analytical Data for Example 10:

N-(2,6-Diisopropylphenyl)quaterrylene-3,4-dicarboximide: elemental analysis (% by weight calc./found): C: 88.85/88.9; H: 4.85/4.8; N: 1.9/1.9; O: 4.4/4.4; mass (FD, 8 kV): m/e=729.3 ($M^+$, 100%); IR (KBr): ν=1690 (s, C=O), 1651 (s, C=O) $cm^{-1}$; UV/VIS (NMP): $\lambda_{max}$ (ε)=677 (72355), 740 (80001) nm.

C) Preparation of 11-bromoterrylene-3,4-dicarboximides and 13-bromoquaterrylene-3,4-dicarboximides I According to the Invention ($R^1$=Br)

Examples 13 to 18 x g (0.1 mol) of rylene derivative I were suspended in 1.5 l of glacial acetic acid for 30 minutes. After 1 g (3.9 mmol) of iodine and 64 g (0.4 mol) of bromine had been added, the mixture was stirred at T° C. for t hours with exclusion of light.

The reaction mixture was subsequently freed from excess bromine by passing a vigorous stream of nitrogen through

TABLE 2

| Ex. | x [g] | Rylenetetracarboxylic monoimide monoanhydride III | t [h] | Yield [g]/[%] | Appearance | m.p. [° C.] |
|---|---|---|---|---|---|---|
| 7 | 4.8 | N-(2,6-Diisopropylphenyl)terrylene-3,4:11,12-tetracarboxylic monoimide monoanhydride | 10 | 3.7/88 | Bluish black, microcrystalline | >350 |
| 8 | 4.4 | N-(p-Methoxyphenyl)terrylene-3,4:11,12-tetracarboxylic monoimide monoanhydride | 12 | 3.3/85 | Blue-black, crystalline | >350 |
| 9 | 4.8 | N-Dodecylterrylene-3,4:11,12-tetracarboxylic monoimide monoanhydride | 15 | 3.9/90 | Black, amorphous | >350 |
| 10 | 5.6 | N-(2,6-Diisopropylphenyl)quaterrylene-3,4:13,14-tetracarboxylic monoimide monoanhydride | 15 | 4.1/80 | Black, microcrystalline | >350 |
| 11 | 5.2 | N-(p-Methoxyphenyl)quaterrylene-3,4:13,14-tetracarboxylic monoimide monoanhydride | 20 | 4.3/90 | Black, microcrystalline | >350 |
| 12 | 5.7 | N-Dodecylquaterrylene-3,4:13,14-tetracarboxylic monoimide monoanhydride | 20 | 4.4/86 | Black, amorphous | >350 |

Analytical Data for Example 7

N-(2,6-Diisopropylphenyl)terrylene-3,4-dicarboximide: elemental analysis (% by weight calc./found): C: 87.25/87.4; H: 5.15/5.2; N: 2.3/2.2; O: 5.3/5.2; mass (FD, 8 kV): m/e=605.2 ($M^+$, 100%); IR (KBr): ν=1687 (s, C=O), 1647 (s, C=O) $cm^{-1}$; UV/VIS (NMP): $\lambda_{max}$ (ε)=580 (42933), 639 (47376) nm.

the mixture, then diluted with 1 l of methanol and stirred overnight at room temperature.

The precipitated product was filtered off, washed firstly with 1.5 l of methanol and then with water until the washings were neutral, and dried at 120° C. under reduced pressure.

Further details on these experiments and their results are shown in Table 3.

TABLE 3

| Ex. | x [g] | Rylene derivatives I | t [h] | T [° C.] | Yield [g]/[%] | Appearance | m.p. |
|---|---|---|---|---|---|---|---|
| 13 | 60.6 | N-(2,6-Diisopropylphenyl)terrylene-3,4-dicarboximide | 8 | 30 | 61.6/90 | Dark blue, crystalline | >350 |
| 14 | 55.2 | N-(p-Methoxyphenyl)terrylene-3,4-dicarboximide | 12 | 40 | 56.7/90 | Dark blue, microcrystalline | >350 |
| 15 | 61.4 | N-Dodecylterrylene-3,4-dicarboximide | 8 | 30 | 61.0/88 | Dark blue, microcrystalline | >350 |
| 16 | 73.0 | N-(2,6-Diisopropylphenyl)quaterrylene-3,4-dicarboximide | 12 | 35 | 68.7/85 | Blue-green, crystalline | >350 |
| 17 | 67.6 | N-(p-Methoxyphenyl)quaterrylene-3,4-dicarboximide | 16 | 40 | 67.9/90 | Blue-green, microcrystalline | >350 |
| 18 | 73.8 | N-Dodecylquaterrylene-3,4-dicarboximide | 12 | 35 | 67.0/82 | Blue-green crystalline | >350 |

Analytical Data for Example 13

11-Bromo-N-(2,6-diisopropylphenyl)terrylene-3,4-dicarboximide: elemental analysis (% by weight calc./found): C: 77.2/77.0; H: 4.4/4.4; N: 2.05/2.1; O: 4.7/4.7; Br: 11.7/11.8; mass (FD, 8 kV): m/e=684.6 (M$^+$, 100%); IR (KBr): ν=1686 (s, C=O), 1645 (s, C=O) cm$^{-1}$; UV/VIS (NMP): $\lambda_{max}$ (ε)=578 (46018), 643 (52323) nm.

Analytical Data for Example 16

13-Bromo-N-(2,6-diisopropylphenyl)quaterrylene-3,4-dicarboximide: elemental analysis (% by weight calc./found): C: 80.2/80.5; H: 4.2/4.2; N: 1.7/1.7; O: 4.0/4.1; Br: 9.9/9.5; mass (FD, 8 kV): m/e=808.7 (M$^+$, 100%); IR (KBr): ν=1689 (s, C=O), 1650 (s, C=O) cm$^{-1}$; UV/VIS (NMP): $\lambda_{max}$ (ε)=671 (80081), 748 (88256) nm.

We claim:

1. A rylene derivative of formula Ia or formula Ib:

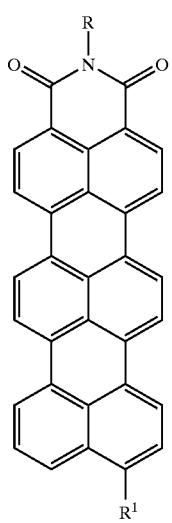

Ia

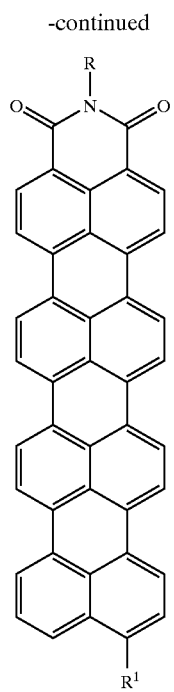

Ib where the variables have the following meanings:

R is hydrogen;

$C_1$–$C_{30}$-alkyl, whose carbon chain may be interrupted by one or more —O—, —S—, —NR$^2$—, —CO— and/or —SO$_2$— groups and which may be monosubstituted or polysubstituted by carboxyl, sulfo, hydroxyl, cyano, $C_1$–$C_6$-alkoxy and/or by a 5- to 7-membered heterocyclic radical which is bonded via a nitrogen atom, may contain further heteroatoms and may be aromatic;

aryl or hetaryl, each of which may be monosubstituted or polysubstituted by $C_1$–$C_{18}$-alkyl, $C_1$–$C_6$-alkoxy, halogen, hydroxyl, cyano, carboxyl, —CONHR$^3$, —NHCOR$^3$ and/or aryl- or hetarylazo, each of which may be substituted by $C_1$–$C_1$-alkyl, $C_{10}$–$C_6$-alkoxy, halogen, hydroxyl, cyano and/or carboxyl;

R$^1$ is hydrogen or bromine;

R$^2$ is hydrogen or $C_1$–$C_6$-alkyl;

R$^3$ is hydrogen; $C_1$–$C_{18}$-alkyl; aryl or hetaryl, each of which may be substituted by $C_1$–$C_8$-alkyl, $C_2$–$C_6$-alkoxy, halogen, hydroxyl and/or cyano.

2. A rylene derivative of formula Ia or Ib of claim 1, where the variables have the following meanings:

R is $C_1$–$C_{30}$-alkyl, whose carbon chain may be interrupted by one or more —O—, —S—, —NR$^2$—, —CO— and/or —SO$_2$— groups and which may be monosubstituted or polysubstituted by hydroxyl, cyano, $C_1$–$C_6$-alkoxy and/or by a 5- to 7-membered heterocyclic radical which is bonded via a nitrogen atom, may contain further heteroatoms and may be aromatic;

aryl or hetaryl, each of which may be monosubstituted or polysubstituted by $C_1$–$C_{18}$-alkyl, $C_1$–$C_6$-alkoxy, hydroxyl, cyano, —CONHR$^3$ and/or —NHCOR$^3$;

R$^1$ is hydrogen or bromine;

R$^2$ is hydrogen or $C_1$–$C_6$-alkyl;

R$^3$ is hydrogen; $C_1$–$C_{18}$-alkyl; aryl or hetaryl, each of which may be substituted by $C_1$–$C_8$-alkyl, $C_1$–$C_6$-alkoxy or cyano.

3. A process for the preparation of a rylene derivative of formula Ia or Ib of claim 1, which comprises a) monohydrolyzing an asymmetrical rylenetetracarboxylic diimide of the formula IIa or IIb

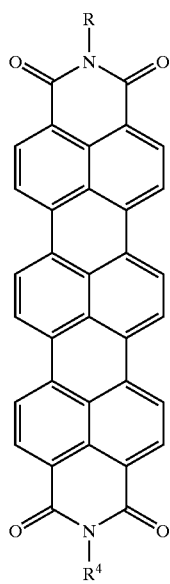

IIa

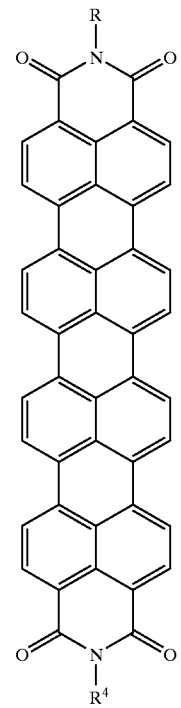

IIb where R$^4$ is $C_5$–$C_8$-cycloalkyl, whose carbon skeleton may be interrupted by one or more —O—, —S— and/or —NR$^2$— groups and which may be monosubstituted or polysubstituted by $C_1$–$C_6$-alkyl, under alkaline conditions in the presence of a polar organic solvent, b) monodecarboxylating the rylenetetracarboxylic monoimide monoanhydride of the formula IIIa or IIIb

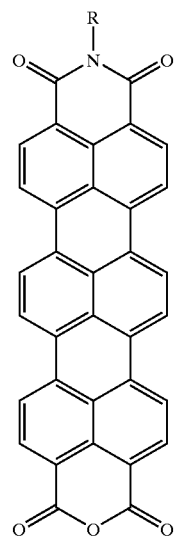

IIIa

-continued

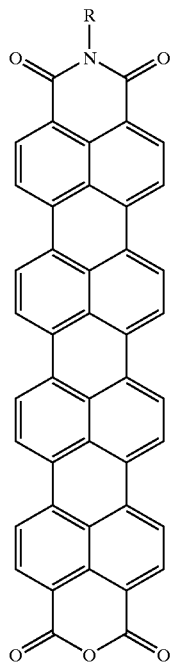

IIIb formed in step a) in the presence of a tertiary nitrogen-basic compound and in the presence of a transition-metal catalyst, and c) optionally, subsequently reacting the reaction product with elemental bromine.

4. A method for coloring high-molecular-weight organic or inorganic materials comprising contacting the materials with the rylene derivative of formula Ia or Ib of claim 1.

5. The method of claim 4, wherein the materials are plastics, surface coatings, printing inks or oxidic layer systems.

6. A dispersion aid, pigment additive for organic pigment or intermediate for the preparation of fluorescent colorants and pigment additives comprising the rylene derivative of formula Ia or Ib of claim 1.

7. A coloring component in decorative cosmetics comprising the rylene derivative of formula Ia or Ib of claim 1.

8. An aqueous polymer dispersion which is colored or absorbs and/or emits in the near infrared region of the electromagnetic spectrum comprising a dispersed polymer, water, and the rylene derivative of formula Ia or Ib of claim 1.

9. A photoconductor in electrophotography comprising the rylene derivative of formula Ia or Ib of claim 1.

10. An emitter in electroluminescence or chemiluminescence comprising the rylene derivative of formula Ia or Ib of claim 1.

11. An active component in fluorescence conversion comprising the rylene derivative of formula Ia or Ib of claim 1.

12. A laser dye comprising the rylene derivative of formula Ia or Ib of claim 1.

* * * * *